United States Patent
Lu et al.

(10) Patent No.: US 8,131,334 B2
(45) Date of Patent: Mar. 6, 2012

(54) INTRA-BODY COMMUNICATION (IBC) DEVICE AND A METHOD OF IMPLEMENTING THE IBC DEVICE

(75) Inventors: Shey-Shi Lu, Taipei (TW); Yu-Tso Lin, Taipei (TW); Chun-Hao Chen, Taipei (TW); Kai-Wen Yeh, Taipei (TW)

(73) Assignee: National Taiwan University, Taipei (TW)

( * ) Notice: Subject to any disclaimer, the term of this patent is extended or adjusted under 35 U.S.C. 154(b) by 769 days.

(21) Appl. No.: 12/236,804

(22) Filed: Sep. 24, 2008

(65) Prior Publication Data

US 2009/0240131 A1    Sep. 24, 2009

(30) Foreign Application Priority Data

Mar. 18, 2008 (TW) ............................... 97109471 A

(51) Int. Cl.
*H04B 5/02* (2006.01)
*A61B 5/04* (2006.01)
(52) U.S. Cl. ... 600/372; 439/909; 455/41.1; 340/539.12
(58) Field of Classification Search .................. 600/372, 600/382, 393, 509, 547; 439/909; 340/539.12; 455/41.1; 128/903
See application file for complete search history.

(56) References Cited

U.S. PATENT DOCUMENTS

| | | | | |
|---|---|---|---|---|
| 5,914,701 A * | 6/1999 | Gersheneld et al. | ......... | 345/156 |
| 6,561,978 B1 * | 5/2003 | Conn et al. | ........... | 600/309 |
| 6,771,161 B1 * | 8/2004 | Doi et al. | ........... | 340/5.64 |
| 6,942,615 B2 * | 9/2005 | Suzuki et al. | ........... | 600/300 |
| 2003/0139783 A1 * | 7/2003 | Kilgore et al. | ........... | 607/49 |
| 2008/0262376 A1 * | 10/2008 | Price | ........... | 600/547 |

OTHER PUBLICATIONS

Microchip Technology Inc. "Specifications for PIC16F877" (2003) available at http://www.microchip.com/wwwproducts/devices.aspx?ddocname=en010241.*
Zimmerman, "Personal Area Networks (PAN): Near-Field Intra-Body Communication" Masters Thesis, Massachusetts Institute of Technology (1995).*
"Development and Performance Analysis of Intra-Body Communication Device," Hachisuka et al., The 12th Int. Conference on Solid State Sensors, Actuators and Microsystems , pp. 1722-1725, Jun. 2003.
"A Near-Field-Sensing Transceiver for Intrabody Communication Based on The Electrooptic Effect," Shinagawa et al., IEEE trans. on instrumentation and measurement, pp. 1533-1538, vol. 53, No. 6, Dec. 2004.

* cited by examiner

*Primary Examiner* — Lee Cohen
*Assistant Examiner* — Erin M Cardinal
(74) *Attorney, Agent, or Firm* — Morris Manning & Martin LLP; Tim Tingkang Xia, Esq.

(57) ABSTRACT

The present invention relates to an intra-body communication (IBC) device and a method of implementing the IBC device. The IBC device is fabricated as a system-on-a-chip (SOC) and comprises a first electrode, a second electrode, an IBC module and a biomedical chip. The first electrode is connected to a patient's skin. The second electrode is connected to the patient's skin. The IBC module is connected to the first electrode and comprises a wireless communication device. The biomedical chip is connected to the second electrode and communicates with the IBC module through the patient's skin to receive external commands and transmit sensed biomedical parameters to a faraway location.

18 Claims, 6 Drawing Sheets

INTRA-BODY COMMUNICATION (IBC) DEVICE AND A METHOD OF IMPLEMENTING THE IBC DEVICE

FIELD OF THE INVENTION

The present invention relates to an intra-body communication (IBC) device, and more particularly to an IBC device designed and fabricated as a system-on-a-chip (SOC) and the method of implementing the IBC.

BACKGROUND OF THE INVENTION

With rapid progresses of communication and semiconductor technology development, wireless sensor networks are used in the biomedical information field and related applications. Rather than interacting directly with a patient to obtain a diagnosis, doctors can use wireless sensors and the IBC technology, coupled with electrical devices for detecting and analyzing patients' physiological conditions. There are three methodologies to implement IBC technology, and one of them uses a patient's body and a conducting wire. The patient's body is used as a conductor. The conducting wire serves as a grounding conductor to form a circuit loop. The other way uses an electrostatic coupling method proposed by Zimmerman and does not employ a conducting wire. However, transfer efficiency is easily affected by the environment, and the transmission speed is slow. Another way uses a guided wave to transmit information and the communication quality is less influenced by environmental factors.

In 2003, Hachisuka et al. reported a FM/ASK hybrid transceiver with a carrier frequency of 10 MHz. However, the device is suffered from low data rate, which was about 9.6 kbps, and low integration level (Development and performance analysis of an Intra-body communication device. *The 12th Int. Conference on Solid state sensors Actuators, and Microsystem.* 1722-1725. June 2003).

Shinagawa et al. proposed a high data rate (10 Mbps) near-field sensing hybrid transceiver for IBC based on the electro-optic effect in 2004. However, it had drawbacks of low integration rate, high power consumption and large form factor (A near-field-sensing hybrid transceiver for IBC based on the electro-optic effect. *IEEE trans.* on instrumentation and measurement. 53(6): 1533-1538).

Drawbacks with lower integration level and slow data rate in the foregoing communication devices result in difficulty in real applications. Therefore, it is important to construct a small, light and minimized IBC device as a SOC.

SUMMARY OF THE INVENTION

The main objective of the present invention is to provide a light and minimized intra-body communication (IBC) device and a method of implementing the IBC device.

The present invention relates to an intra-body communication (IBC) device and a method of implementing the IBC device. The IBC device is fabricated as a system-on-a-chip (SOC) and comprises a first electrode, a second electrode, an IBC module and a biomedical chip. The first electrode is connected to a patient's skin. The second electrode is connected to the patient's skin. The IBC module is connected to the first electrode and comprises a wireless communication device. The biomedical chip is connected to the second electrode and communicates with the IBC module through the patient's skin to receive external commands and transmit sensed biomedical parameters to a remote location.

BRIEF DESCRIPTION OF THE DRAWINGS

Many attendant advantages and features of this invention will become more apparent by reference to the following detailed description, when taken in conjunction with the accompanying drawings, wherein.

DETAILED DESCRIPTION OF THE PRESENT INVENTION

Figure 1:
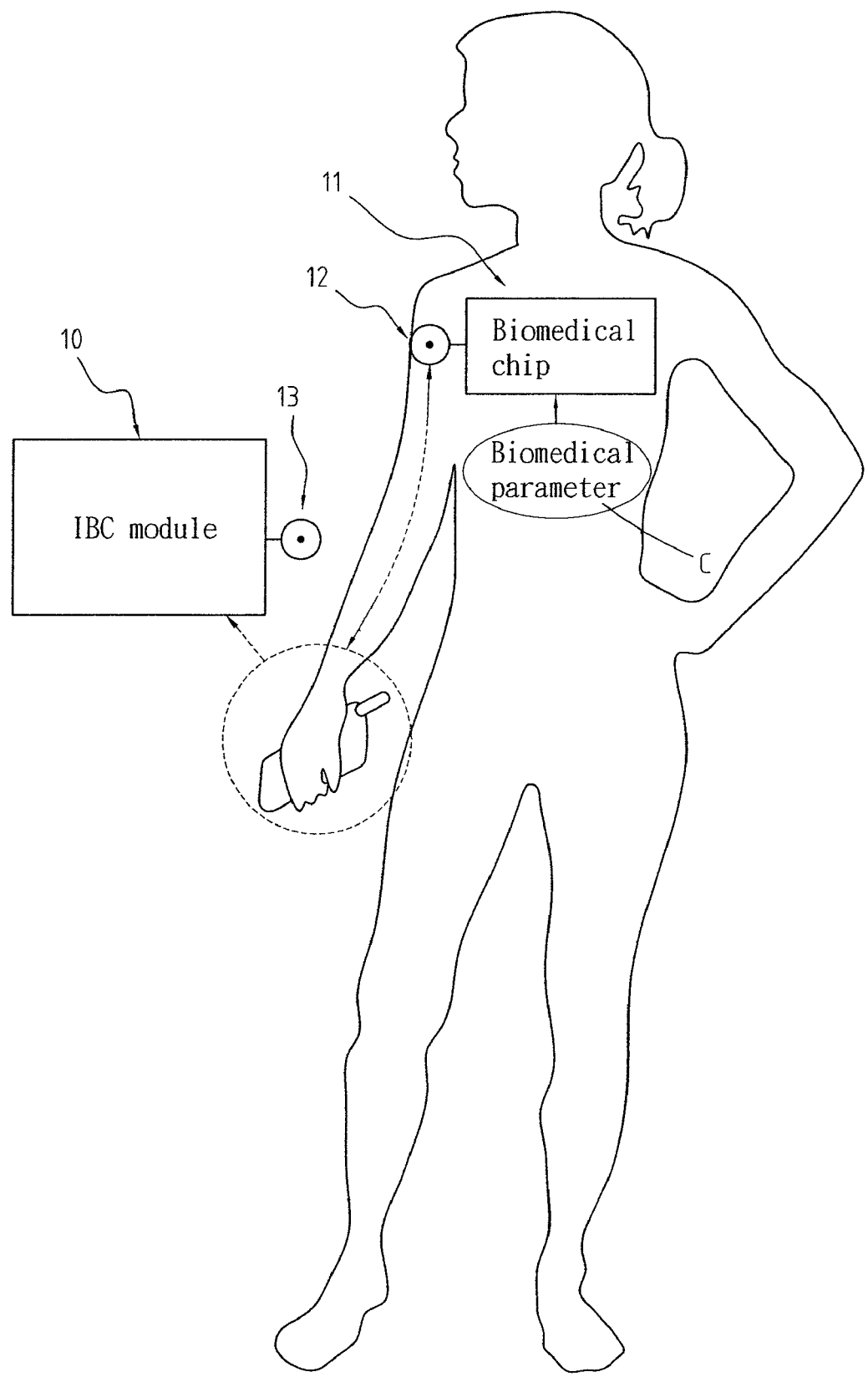
FIG. 1 is an operational diagram of an intra-body communication (IBC) device in accordance with the present invention attached to a person's body.
Figure 2:
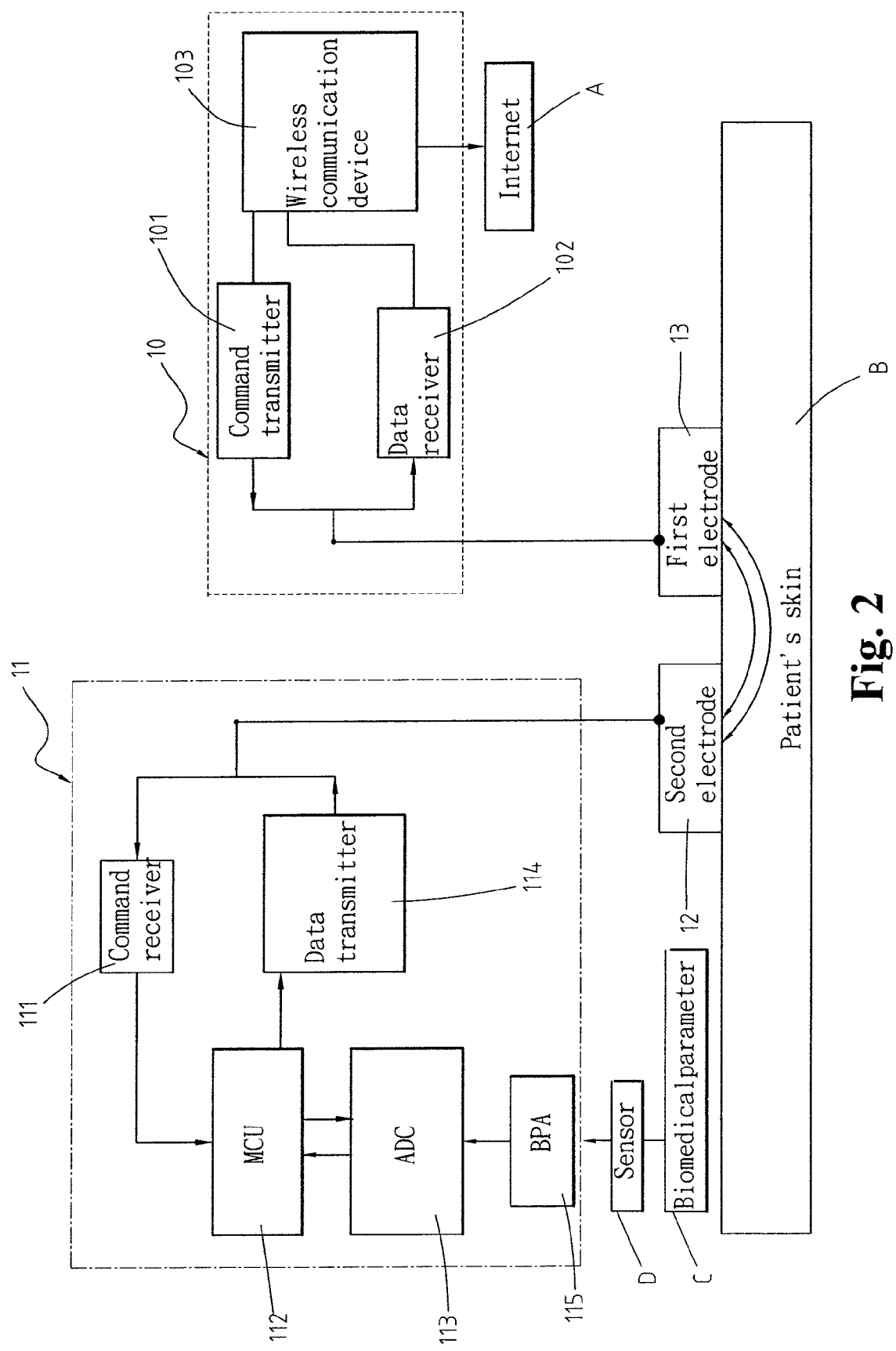
FIG. 2 is a block diagram of the IBC device in FIG. 1.

With reference to FIGS. 1 and 2, an intra-body communication (IBC) device and a method of implementing the IBC device in accordance with the present invention are used in remote monitoring of a patient's biomedical parameters.

The IBC device is designed and fabricated as a system-on-a-chip (SOC), may have a transmission rate of 2 Mbps, may use a driving voltage of 0.5V and comprises a first electrode (13), a second electrode (12), an IBC module (10) and a biomedical chip (11).

The first electrode (13) may be a silver (Ag) or silver chloride (AgCl) and has an inner end and an outer end. The outer end connects detachably to a patient's skin (B).

The second electrode (12) may be a silver (Ag) or silver chloride (AgCl) electrode and has an inner end and an outer end. The outer end connects detachably to the patient's skin (B).

The IBC module (10) is connected to the inner end of the first electrode (13), receives an external command, transmits the external command, receives patient information, transmits the patient's biomedical parameters (C) and comprises a command transmitter (101), a data receiver (102) and a wireless communication device (103).

The command transmitter (101) is connected to the inner end of the first electrode (13) and transmits the external command to the second electrode (12) through the first electrode (13) and the patient's skin (B).

The data receiver (102) is connected to the inner end of the first electrode (13) and receives patient biomedical parameters (C) from the second electrode (12) through the patient's skin (B) and the first electrode (13).

The wireless communication device (103) is connected to the command transmitter (101) and data receiver (102), is a wireless transceiver, receives commands from external sources, sends commands to the command transmitter (101) and receives, modulates and transmits patient biomedical parameters (C) to an external recipient and may be a dedicated transceiver, a cellular phone, a watch, a personal digital assistant (PDA) or a pager. The commands from external sources may be received via internet (A), a cellular phone network or any other conventional communication media. The patient biomedical parameters (C) may be transmitted via internet (A), a cellular phone or any other conventional communication media.

The biomedical chip (11) is connected to the inner end of the second electrode (12) and a biomedical parameter sensor (D), receives activation commands from the IBC module (10), samples patient biomedical parameters (C) sensed by the biomedical parameter sensor (D), amplifies, converts, modulates and transmits the patient biomedical parameters (C) to the IBC module (10) through the second electrode (12), a patient's skin (B) and the first electrode (13), the biomedical chip (11) comprises a command receiver (111), a microcontrol unit (MCV) (112), an analog-to-digital converter (ADC) (113), a data transmitter (114) and a biomedical parameter amplifier (BPA) (115) and may be implemented in a 0.18μm CMOS technology, and has chip size of 1.5mm$^2$.

Figure 3:
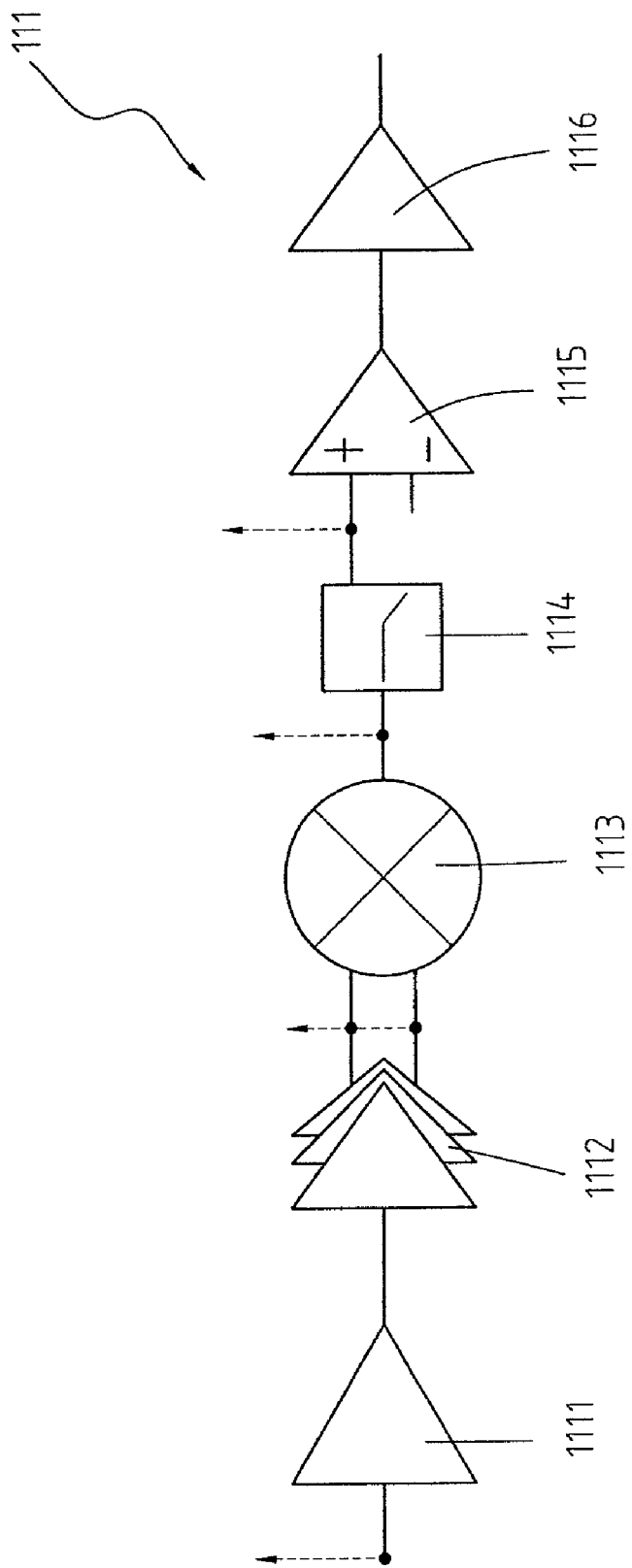
FIG. 3 is circuit diagram of a receiver in a biomedical chip in the IBC device in FIG. 2.

With further reference to FIG. 3, the command receiver (111) is connected to the inner end of the second electrode (12), receives commands from the IBC module (10), may be a self-mixing receiver that is an on/off shift keying circuit and may comprise a low voltage amplifier (LVA) (1111), a cascaded gain amplifier (1112), a low voltage multiplier (LVM) (1113), a low pass filter (LPF) (1114), a comparator (1115) and a buffer (1116). The LVA (1111) amplifies a received signal. The cascaded gain amplifier (1112) is connected to the LVA (1111) and further amplifies the signal. The LVM (1113) is connected to the cascaded gain amplifier (1112) and multiplies the two amplified signals to form a multiplied signal. The LPF (1114) is connected to the LVM (1113) and filters the multiplied signal to produce a DC signal. The comparator (1115) is connected to the LPF (1114) and converts the DC signal output from the LPF (1114) to a digital signal. The buffer (1116) is connected to the comparator (1115) and holds the digital signal output from the comparator (1115).

Figure 4:
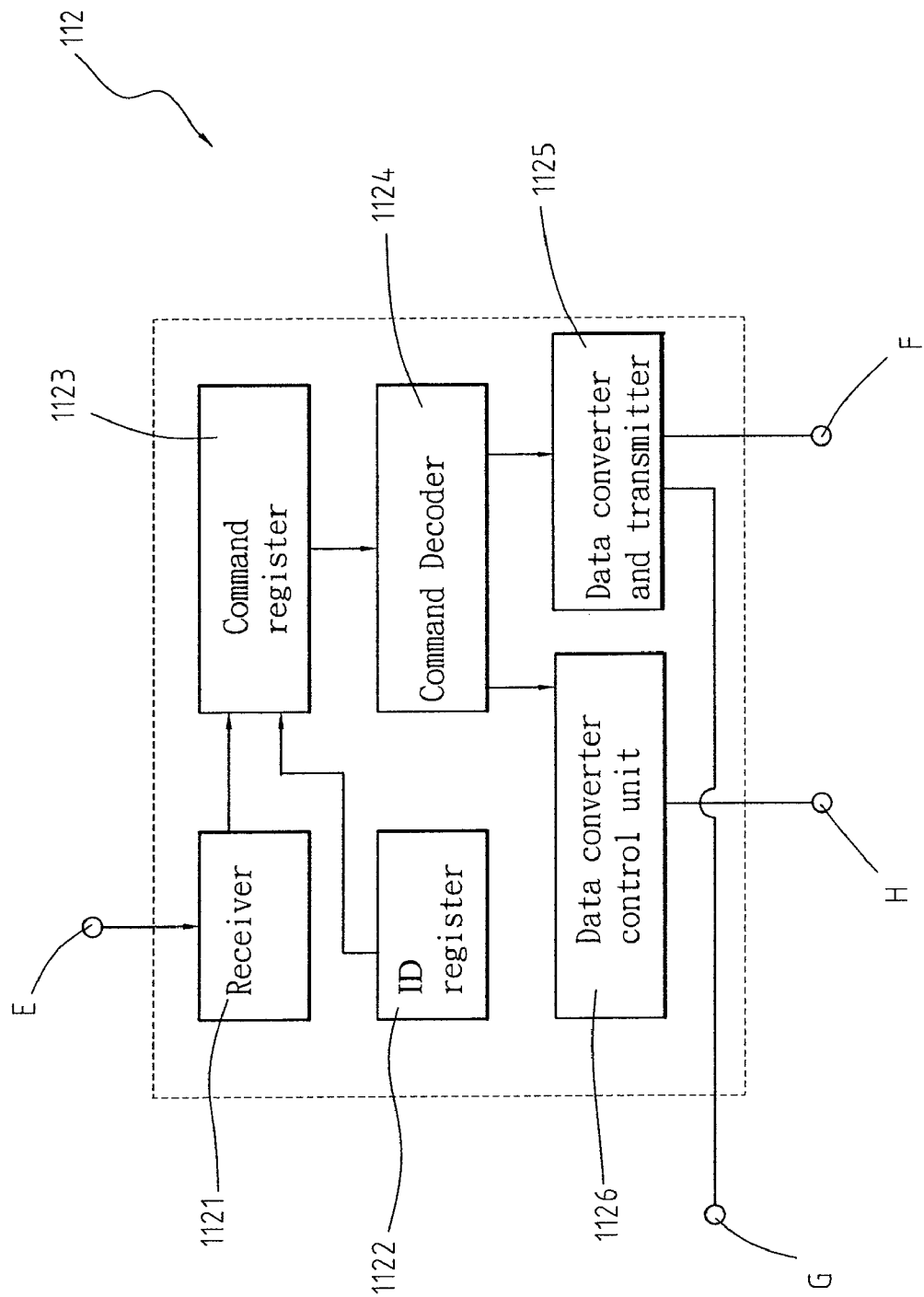
FIG. 4 is a functional block diagram of a micro-control unit in the IBC device in FIG. 2.

With further reference to FIG. 4, the MCU (112) is connected to the command receiver (111), processes commands from the IBC module (10), may use an RS-232 specification in formatting commands, controls operation of the biomedical chip (11) and is a Universal Asynchronous Receiver Transmitter (UART) that receives an external signal, controls data transmission and may comprise a receiver (1121), an ID register (1122), a command register (1123), a command decoder (1124), a data converter and transmitter (1125) and a data converter control unit (1126).

The receiver (1121) has a signal input terminal (E), is connected to the command receiver (111) at the signal input terminal (E) and receives signals from the command receiver (111).

The ID register (1122) holds authorized commands.

The command register (1123) is connected to the receiver (1121) and the ID register (1122), holds coded commands corresponding to the authorized commands in the ID register (1122), compares signals received from the command receiver (111) with authorized commands in the ID register (1122) and transmits the coded command when the signal corresponds to an authorized command in the ID register (1122).

The command decoder (1124) is connected to the command register (1123) and further decodes coded commands received from the command register (1123).

The data converter and transmitter (1125) is connected to and enabled by the command decoder (1124), may convert parallel data to serial data and has a data output terminal (F) and a data input terminal (G).

The data converter control unit (1126) is connected to the command decoder (1124) and has an output terminal (H).

The ADC (113) is connected to the MCU (112) at the output terminal (H) of the data converter control unit (1126), is enabled by a signal from the MCU (112) and converts analog patient biomedical parameter signals from the biomedical parameter sensor (D) to digital patient biomedical parameter signals.

Figure 5:
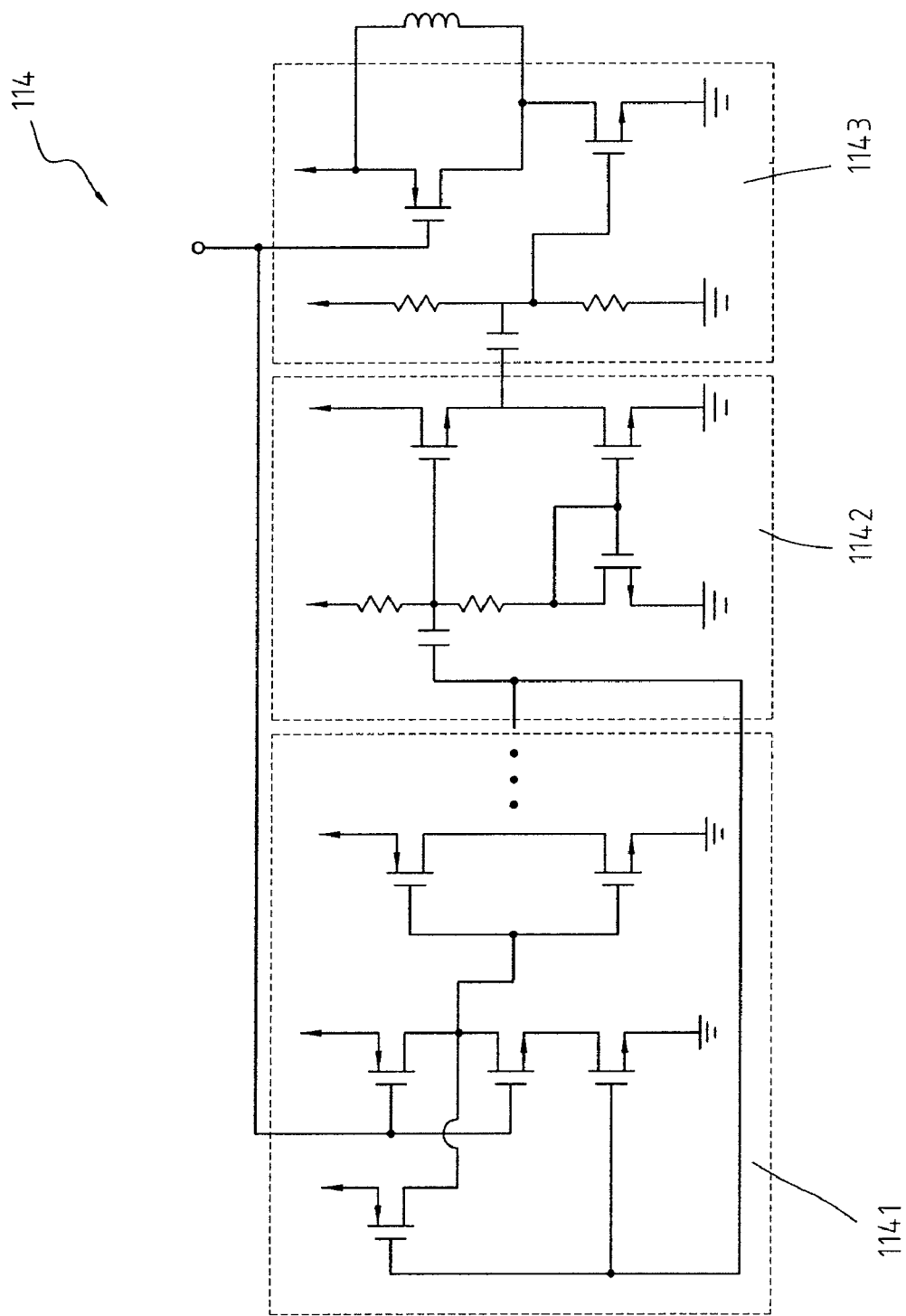
FIG. 5 is a circuit diagram of a data transmitter of the biomedical chip in FIG. 2.
Figure 6:
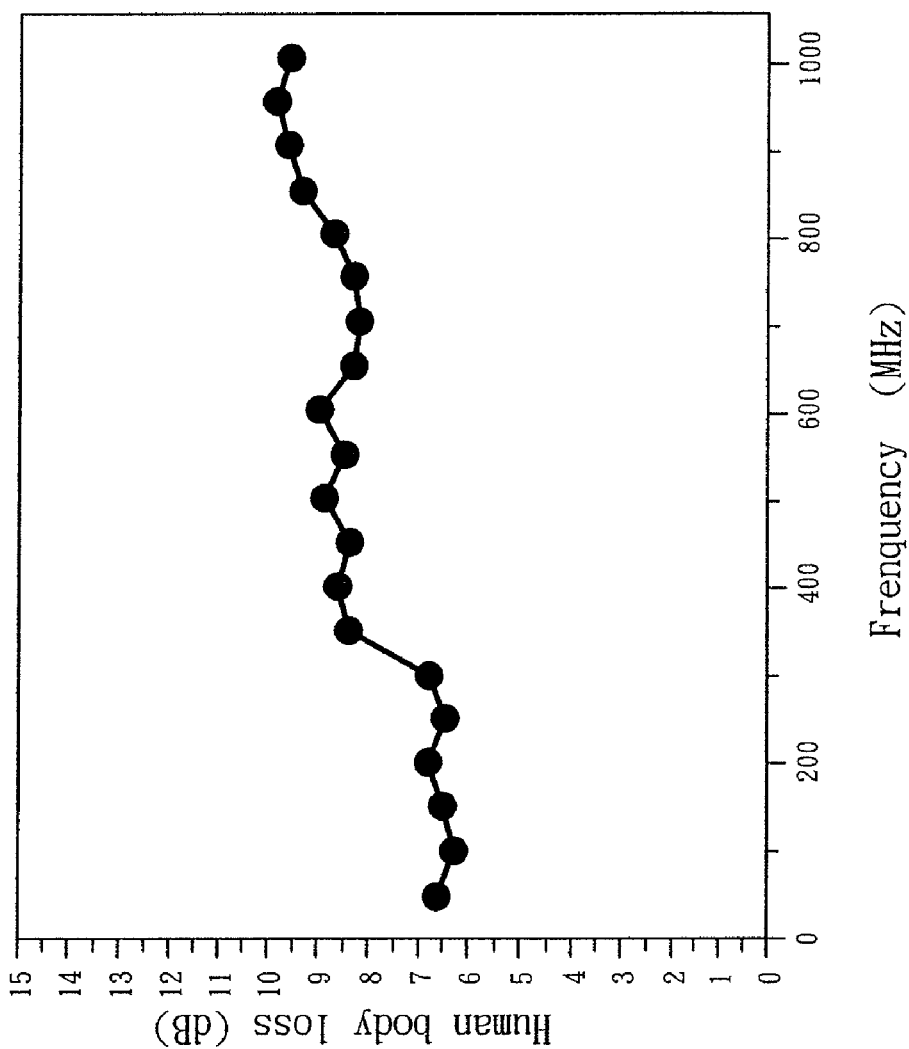
FIG. 6 is a graph of signal loss through a human body in FIG. 2.

With further reference to FIG. 5, the data transmitter (114) is connected to and enabled by the MCU (112), connects to the inner end of the second electrode (12) to provide a data path to the IBC module (10), modulates and transmits digital patient biomedical parameter signals to the IBC module (10), is an on/off shift keying circuit and may comprise a ring-oscillator (1141), a buffer (1142) and a class-C power amplifier (1143). The ring-oscillator (1141) is operated to produce signals in a frequency range of 50 to 200 MHz. With further reference to FIG. 6, human skin acts as a low-pass filter with a bandwidth of 200 MHz and the signals only experience a 7 dB transmission loss through the human skin. The class-C power amplifier (1143) promotes an improved data transmission rate by being turned on/ff and comprises a surface-mounted-device (SMD), an n-MOSFET transistor and a P-MOSFET transistor.

The BPA (115) is connected to the ADC (113) and a biomedical parameter sensor (D), and the BPA amplifies signals from the biomedical parameter sensor (D).

When the commands meet the RS-232 specification, the commands may include but are not be limited to idle, convert, transmit and continue commands. The idle command puts the MCU (112) in an idle or standby mode. The convert command directs the MCU (112) to send an enable signal to turn on the ADC (113) and may also enable the BPA (115). The transmit command causes the MCU (112) to transmit data. The continue command enables the ADC (113) to sample and convert data sensed by the biomedical parameter sensor (D).

The method of implementing an IBC device comprises acts of receiving wireless commands from an external source, initiating sampling of a biomedical parameter sensor (D), amplifying, converting and transmitting sensed biomedical parameters and transmitting the sensed biomedical parameters via wireless means.

The act of receiving wireless commands from an external source comprises receiving activation and mode commands by a wireless communication device (103) such a cellular phone, wireless computer or the like.

The act of initiating sampling of a biomedical parameter sensor (D) comprises enabling an ADC (113) and data transmitter (114) so biomedical parameters sensed by a biomedical parameter sensor (D) attached to a patient can be converted and forwarded to the wireless communication device (103) through a patient's skin for further transmission to a faraway location.

The act of amplifying, converting and transmitting sensed biomedical parameters comprises amplifying analog biomedical parameters sensed by a biomedical parameter sensor (D) attached to a patient, converting the analog biomedical parameters to digital signals and transmitting modulated digital signals through the patient's skin to the wireless communication device.

The act of transmitting the sensed biomedical parameters via wireless means comprises transmitting sensed biomedical parameter to a faraway location by a wireless communication device such as a cellular phone, personal digital assistant (PDA) or the like.

The present invention has numerous advantages. Specifically, the transmission rate and the driving voltage of the present invention allow the design to be further refined to include an alternate power source such as a solar cell. Furthermore, power consumption, approximately 4.3 mW, of the present invention is much lower than conventional devices that transmit unmodulated data. The present invention obviates or mitigates the shortcomings of the prior art including high operating voltage, high power consumption.

Data transmission rate is promoted the class-C power amplifier (1143) by the on/off switching circuitry.

The description is not intended to limit the invention. That various changes, modifications and alterations in form and details may be made without departing from the spirit and scope of the invention, as set forth in the following claims will be understood by those skilled in the art.

What is claimed is:

1. An intra-body communication (IBC) device being designed and fabricated as a system-on-a-chip (SOC) to monitor a patient's biomedical parameters and comprising:
    a first electrode having
        an inner end; and
        an outer end for connecting detachably to the patient's skin;
    a second electrode having
        an inner end; and
        an outer end for connecting detachably to the patient's skin;
    an IBC module being connected to the inner end of the first electrode, receiving an external command, transmitting the external command, receiving the patient's biomedical parameters, transmitting the patient's biomedical parameters and comprising
        a command transmitter being connected to the inner end of the first electrode and transmitting the external command to the second electrode through the first electrode;
        a data receiver being connected to the inner end of the first electrode and receiving patient biomedical parameters from the second electrode through the first electrode;
        a wireless communication device being connected to the command transmitter and data receiver, being a wireless transceiver, receiving commands from external sources, sending commands to the command transmitter and receiving, modulating and transmitting patient biomedical parameters to an external recipient; and
    a biomedical chip being connected to the inner end of the second electrode and a biomedical parameter sensor, receiving activation commands from the IBC module, sampling patient biomedical parameters sensed by the biomedical parameter sensor, amplifying, converting, modulating and transmitting the patient biomedical parameters to the IBC module through the second electrode and the first electrode and comprising
        a command receiver being connected to the inner end of the second electrode and receiving commands from the IBC module;
        a micro-control unit (MCU) comprising a data converter control unit and being connected to the command receiver, processing commands from the IBC module, controlling operation of the biomedical chip, being a Universal Asynchronous Receiver Transmitter (UART) that receives an external signal and controlling data transmission;
        an analog-to-digital converter (ADC) being connected to the MCU, being enabled by a signal from the MCU and for converting analog biomedical patient biomedical parameter signals from the biomedical parameter sensor to digital patient biomedical parameter signals;
        a data transmitter being connected to and enabled by the MCU, connecting to the inner end of the second electrode, modulating and transmitting digital patient biomedical parameter signals to the data receiver of the IBC module and being an on/off shift keying circuit; and
        a biomedical parameter amplifier (BPA) being connected to the ADC and a biomedical parameter sensor and amplifying signals received from the biomedical parameter sensor.

2. The IBC device as claimed in claim 1, wherein the first electrode is silver (Ag).

3. The IBC device as claimed in claim 1, wherein the first electrode is silver chloride (AgCl).

4. The IBC device as claimed in claim 1, wherein the second electrode is silver (Ag).

5. The IBC device as claimed in claim 1, wherein the second electrode is silver chloride (AgCl).

6. The IBC device as claimed in claim 1, wherein the wireless communication device is a dedicated transceiver.

7. The IBC device as claimed in claim 1, wherein the wireless communication device is a cellular phone.

8. The IBC device as claimed in claim 1, wherein the wireless communication device is a personal watch.

9. The IBC device as claimed in claim 1, wherein the wireless communication device is a personal digital assistant.

10. The IBC device as claimed in claim 1, wherein the wireless communication device is a pager.

11. The IBC device as claimed in claim 1, wherein the command receiver is a self-mixing receiver.

12. The IBC device as claimed in claim 11, wherein the command receiver of the biomedical chip comprises
    a low voltage amplifier (LVA) amplifies a received signal;
    a cascaded gain amplifier is connected to the LVA and further amplifies the signal amplified by the LVA to form two amplified signals;
    low voltage multiplier (LVM) is connected to the cascaded gain amplifier and multiplies the two amplified signals to form a multiplied signal;
    a low pass filter (LPF) is connected to the LVM and filters the multiplied signal to form a DC signal;
    a comparator is connected to the LPF and converts the DC signal output from the LPF to a digital signal; and
    a buffer is connected to the comparator and holds the digital signal output from the comparator.

13. The IBC device as claimed in claim 1, wherein the commands from external sources are received via internet; and
    patient biomedical parameters are transmitted via internet.

14. The IBC device as claimed in claim 1, wherein the commands from external sources are received via a cellular phone network; and
    patient biomedical parameters are transmitted via a cellular phone network.

15. The IBC device as claimed in claim 1, wherein the command receiver is an on/off shift keying circuit.

16. The IBC device as claimed in claim 1, wherein the MCU comprises
    a receiver having a signal input terminal, being connected to the command receiver at the signal input terminal and receiving signals from the command receiver;
    an ID register holding authorized commands;
    a command register being connected to the receiver and the ID register, holding coded commands corresponding to the authorized commands in the ID register, comparing signals received from the command receiver with authorized commands in the ID register and transmitting the coded command when the signal corresponds to an authorized command in the ID register;

a command decoder being connected to the command register and further decoding coded commands received from the command register;

a data converter and transmitter being connected to and enabled by the command decoder and having a data output terminal and a data input terminal;

the data converter control unit being connected to the command decoder and having an output terminal; and the ADC is connected to the output terminal of the data converter control unit.

17. The IBC device as claimed in claim 16, wherein the data converter and transmitter converts parallel data to serial data.

18. The IBC device as claimed in claim 1, wherein the data transmitter of the biomedical chip comprises a ring-oscillator being operated to produce signals;

a buffer; and a class-C power amplifier (PA).

* * * * *